United States Patent [19]
Main et al.

[11] Patent Number: 5,261,920
[45] Date of Patent: Nov. 16, 1993

[54] ANVIL BUSHING FOR CIRCULAR STAPLER

[75] Inventors: Lauren O. Main, Loveland, Ohio; Robert F. Welch, Downingtown, Pa.

[73] Assignee: Ethicon, Inc., Somerville, N.J.

[21] Appl. No.: 934,099

[22] Filed: Aug. 21, 1992

[51] Int. Cl.⁵ .............................................. A61B 17/00
[52] U.S. Cl. ................................... 606/153; 606/151; 606/155; 227/19; 227/175
[58] Field of Search ....................... 227/175-176, 227/178-181, 19; 606/151, 153, 155, 156, 213, 215, 219, 220

[56] References Cited

U.S. PATENT DOCUMENTS

| | | | |
|---|---|---|---|
| 3,836,061 | 9/1974 | Grunwald | 227/19 |
| 4,476,863 | 10/1984 | Kanshin et al. | 606/153 |
| 4,592,354 | 6/1986 | Rothfuss | 606/153 |
| 4,703,887 | 11/1987 | Clanton et al. | 227/19 |
| 4,964,863 | 10/1990 | Kanshin et al. | 606/153 |
| 5,188,638 | 2/1993 | Tzakis | 227/178 |

FOREIGN PATENT DOCUMENTS 1509052 9/1989 U.S.S.R. ............................. 227/175

*Primary Examiner*—Stephen C. Pellegrino
*Assistant Examiner*—Jeffrey A. Schmidt

[57] ABSTRACT

An anvil bushing for use with a surgical circular stapler used to perform an anastomosis. The anvil bushing is mounted to the anvil shaft of the stapler. The bushing has a tubular member having an axial pathway therethrough. The tubular member has a proximal end, a distal end and an exterior surface. A first flange member having a first diameter is mounted to the distal end of the tubular member. A second flange member having a second diameter is mounted to the proximal end of the tubular member. The second diameter is larger than the first diameter. Legs for locating the bushing on an anvil shaft extend axially from the first flange member. Tissue notches are contained in the second flange member.

22 Claims, 3 Drawing Sheets

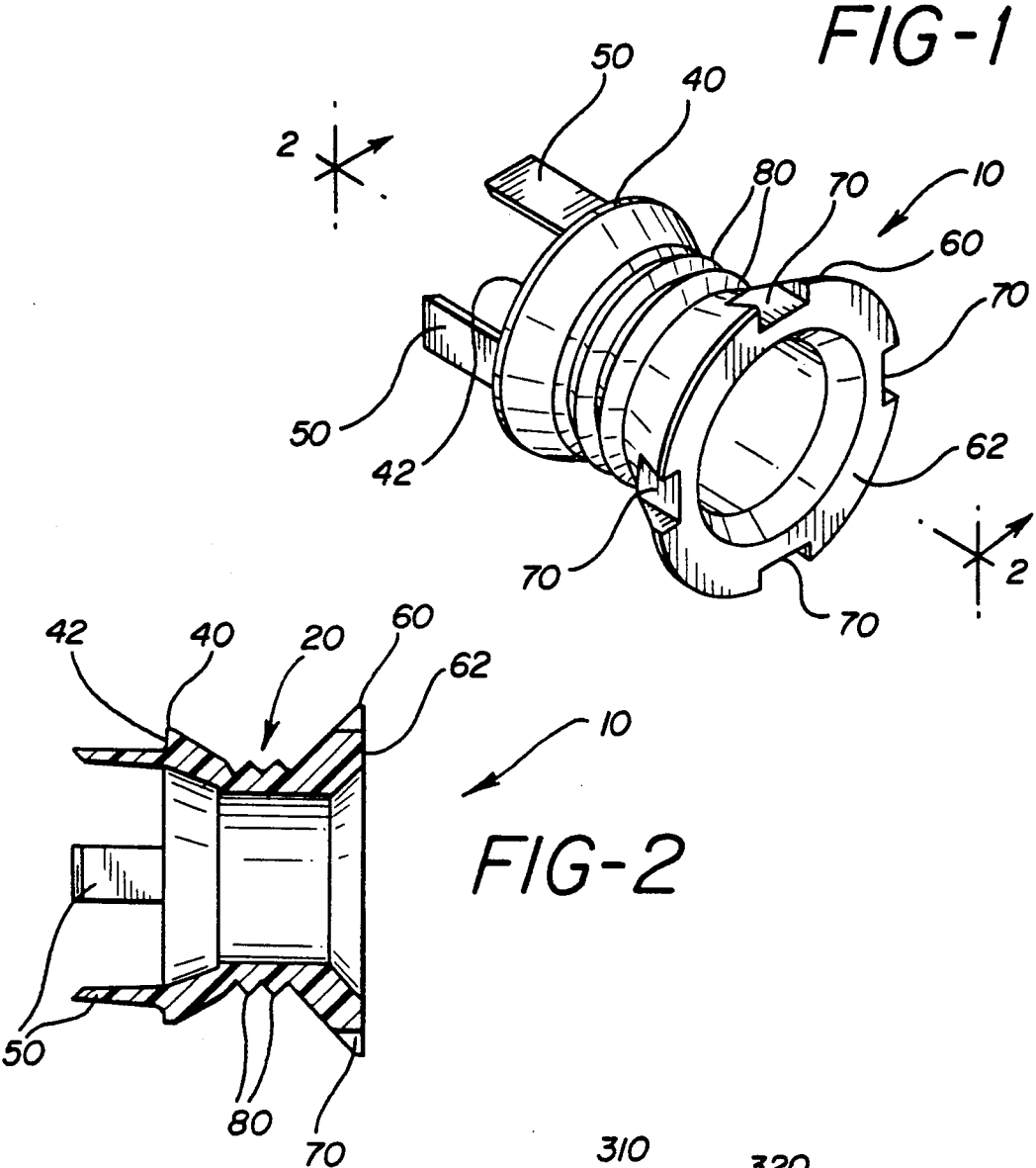
FIG-1
FIG-2
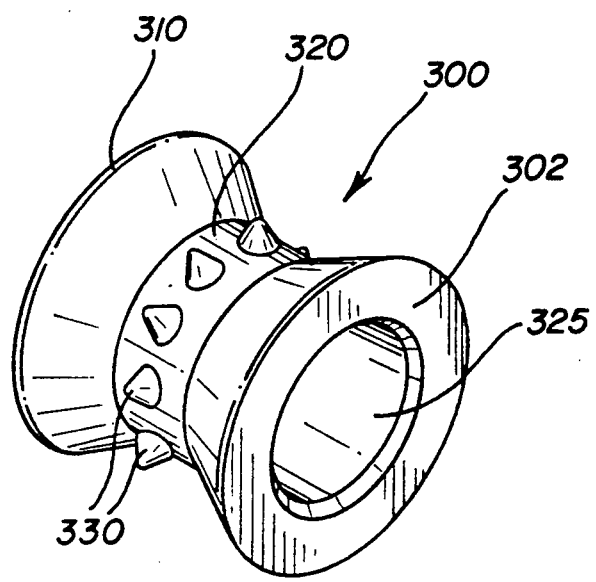
FIG-3
PRIOR ART

ANVIL BUSHING FOR CIRCULAR STAPLER

TECHNICAL FIELD

The field or art to which their invention pertains is surgical instrumentation, in particular, circular surgical staplers.

BACKGROUND OF THE INVENTION

Surgical staplers have been long known in the surgical arts as a quick and efficient way of joining or repairing tissue. Stapling has become an accepted alternative to suturing. In certain types of surgical procedures the use of surgical staples has become the preferred method of joining tissue, and, specially configured surgical staplers have been developed especially for these applications. For example, intraluminal or circular staplers have been developed for use in a surgical procedure known as an anastomosis.

Circular staplers are well known in this art. Circular staplers useful to perform an anastomosis are disclosed in U.S. Pat. No. 5,104,025 which is incorporated by reference. A conventional circular stapler typically consists of an elongated shaft having a proximal actuating mechanism and a distal stapling mechanism mounted to the shaft. The distal stapling mechanism typically consists of a fixed stapling cartridge containing a plurality of staples configured in a concentric circular array. A round cutting knife is concentrically mounted in the cartridge. The knife is moveable in an axial, distal direction. Extending axially from the center of the cartridge is a trocar shaft. The trocar shaft is moveable, axially, with respect to the cartridge and elongated shaft. An anvil member is mounted to the trocar shaft. The anvil member has a conventional staple anvil mounted to it for forming the ends of staples. The distance between the distal face of the staple cartridge and the staple anvil can be controlled by an adjustment mechanism mounted to the proximal end of the stapler shaft. Tissue contained between the staple cartridge and the staple anvil is simultaneously stapled and cut when the actuating mechanism is engaged by the surgeon.

An anastomosis is a surgical procedure wherein sections of intestines are joined together after a connecting section has been excised. The procedure requires joining the ends of two tubular sections together to form a continuous tubular pathway. Previously, this surgical procedure was a laborious and time consuming operation. The surgeon had to precisely cut and align the ends of the intestine and maintain the alignment while joining the ends with numerous suture stitches. The development of circular staplers has greatly simplified the anastomosis procedure and also decreased the time required to perform the anastomosis. When performing an anastomosis using a circular stapler, typically, the intestine is stapled using a conventional surgical stapler with double rows of staples being emplaced on either side of a target section (i.e., specimen) of intestine. The target section is typically simultaneously cut as the section is stapled. Next, the surgeon typically inserts the distal stapling head of the instrument into a section of intestine proximate to a distal staple line. This is done by inserting the distal end of the stapler through the rectum, or by inserting the stapler through an entry port cut into the intestine by the surgeon. The anvil member is then inserted into the intestine adjacent to the proximal staple line. The surgeon then typically ties the proximal end of the intestine to the anvil shaft using a suture or other conventional tying device. Next, the surgeon then cuts excess tissue adjacent to the tie. The surgeon then attaches the anvil to the trocar shaft of the stapler. The surgeon then closes the gap between the anvil and cartridge, thereby engaging the proximal and distal end of the intestine. The surgeon then actuates the stapler causing several rows of staples to be driven through and formed in both ends of the intestine, thereby joining the ends and forming a tubular pathway. Simultaneously, as the staples are driven and formed, a concentric circular blade is driven through the intestinal tissue ends, cutting the ends adjacent to the inner row of staples. The surgeon then withdraws the stapler from the intestine and the anastomosis is complete.

In order to assist the surgeon in performing an anastomosis, various accessories have been developed for use with a circular stapler. One such type of accessory is known as an anvil bushing and is disclosed in U.S. Pat. No. 4,592,354. The anvil bushing disclosed in that patent consists of two flanges separated by a shank member. The shank member has a cylindrical pathway running therethrough. The diameter of the cylindrical pathway is sized so that the spool is in frictional engagement with the anvil shaft. The spool is used as a tissue attachment or retention means wherein intestine is sutured or tied about the spool, and, the intestine may be cut adjacent to the spool.

U.S. Pat. No. 4,665,917 discloses an improved intraluminal stapler having a clamping means disposed on the anvil shaft. The clamping consists of a circular array of barbs extending outwardly to grasp the ends of the intestine.

Although conventional anvil bushings have many advantages and have proven to be beneficial when used with a circular stapler. It is also known that there are disadvantages associated with their use. The anvil bushings must be mounted by the surgeon or an assistant on the anvil shaft prior to use. It is often difficult to precisely position the bushings on the anvil shaft in an optimal position to facilitate tying. It is also known that the presence of the anvil bushing may increase the closing force necessary to position the anvil in proximity to the cartridge to effectively allow stapling and cutting. It is additionally known that it is sometimes difficult to locate the proximal edge of the anvil bushing when the surgeon attempts to cut the intestine. Further, it is also known that the mucosa of the intestine is extremely slippery and that it is difficult to retain the intestine on a conventional anvil bushing.

Therefore, what is needed in this art are improved anvil bushings which facilitate the use of a circular stapler in an anastomotic procedure.

SUMMARY OF THE INVENTION

Accordingly, it is an object of the present invention to provide an anvil bushing for an anastomotic procedure which can be precisely located on an anvil shaft during a surgical anastomotic procedure.

It is yet another object of the present invention to provide an anvil bushing which decreases the force required to close an anvil by providing tissue and fluid venting.

It is yet a further object of the present invention to provide an anvil bushing which facilitates tissue cutting.

It is still a further object of the present invention to provide an anvil bushing which has enhanced tissue grasping and retention.

An anvil bushing for a surgical, circular stapler is disclosed. The bushing comprises a tubular member having a proximal end, a distal end and an exterior surface. The tubular member has an axial passage therethrough, in particular, a cylindrical passageway. A first flange having a first diameter extends from the distal end of the tubular member and a second flange having a second diameter extends from the proximal end of the tubular member. The second diameter is greater than the first diameter. The bushing has tissue notch means in the second flange. Locating means comprising axial legs extend from the first flange.

Another aspect of the present invention is an anvil bushing for a surgical, circular stapler. The bushing comprises a tubular member having a proximal end, a distal end and an exterior surface. The tubular member has an axial passage therethrough, in particular, a cylindrical passageway. A first flange having a first diameter extends from the distal end of the tubular member and a second flange having a second diameter extends from the proximal end of the tubular member. The second diameter is greater than the first diameter.

Yet another aspect of the present invention is an anvil bushing for a surgical, circular stapler. The bushing comprises a tubular member having a proximal end, a distal end and an exterior surface. The tubular member has an axial passage therethrough, in particular, a cylindrical passageway. A first flange having a first diameter extends from the distal end of the tubular member and a second flange having a second diameter is mounted extends from the proximal end of the tubular member. The second diameter is greater than the first diameter. The bushing has tissue notch means in the second flange.

Another aspect of the present invention is the combination of a circular stapler and the above-described anvil bushing.

Yet another aspect of the present invention is a method of using the above described anvil bushing.

BRIEF DESCRIPTION OF THE DRAWINGS

FIG. 1 is a perspective view of the anvil bushing of the present invention.

FIG. 2 is a cross-sectional view of the anvil bushing taken along view line 2—2.

FIG. 3 is a perspective view of an anvil bushing of the prior art.

FIG. 4A is an enlarged partial cross-sectional view of the anvil member of FIG. 4.

DESCRIPTION OF THE PREFERRED EMBODIMENTS

Figure 4:
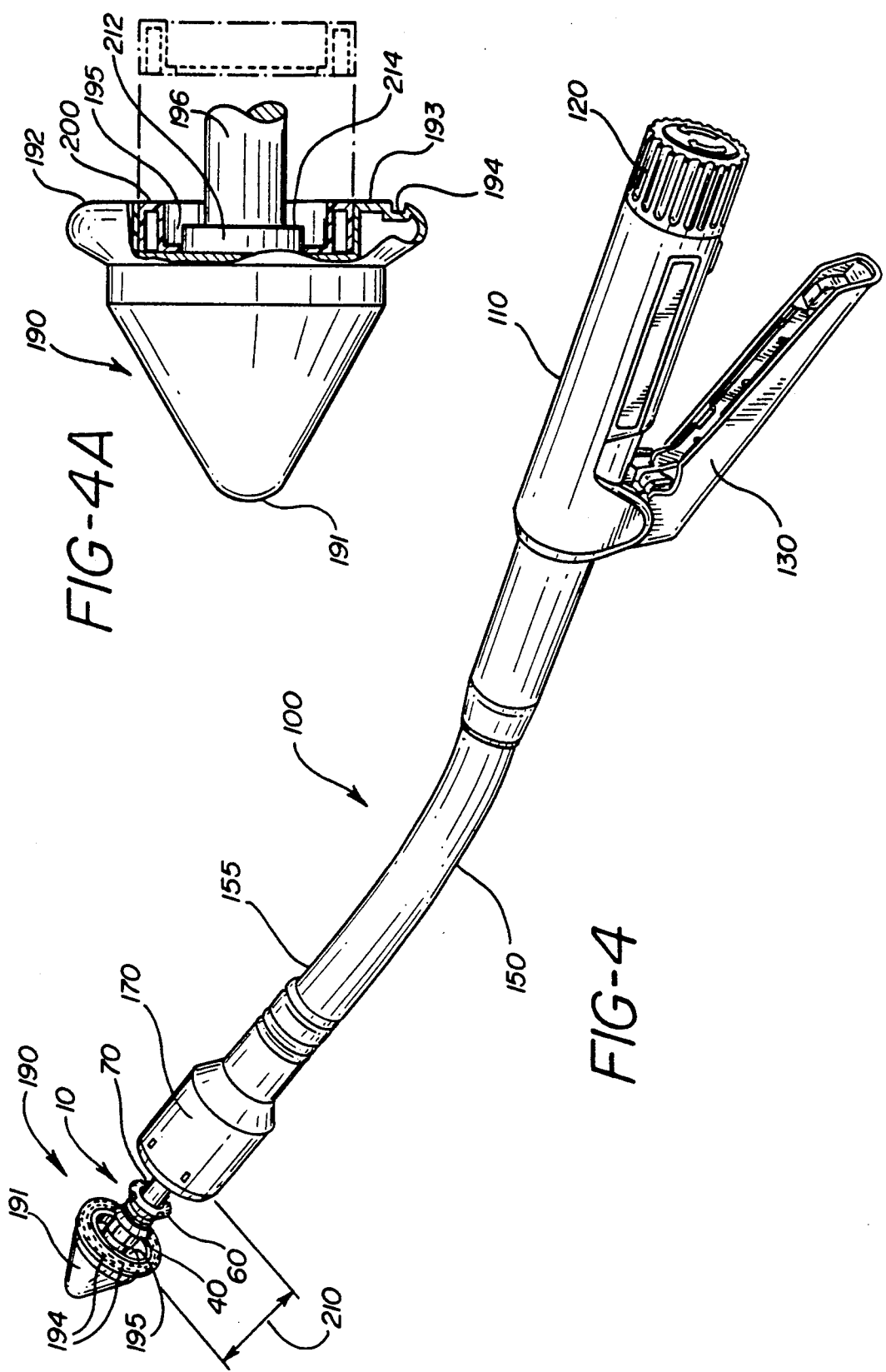
FIG. 4 is a perspective view of the anvil bushing of the present invention mounted to a conventional circular stapler.

The disclosures of U.S. Pat. Nos. 4,592,254 and 4,665,917 are incorporated by reference.

The anvil bushing 10 of the present invention is seen in FIG. 1 and FIG. 2. The anvil bushing 10 is seen to have cylindrical body 20 having pathway 30 therethrough. The pathway 30 preferably has a cylindrical configuration so that it can be easily mounted onto an anvil shaft having a similar cylindrical configuration. Bushing 10 is seen to have first flange 40 extending from the distal end of cylindrical member 20. The first flange 40 is seen to have flat face 42. Spacing legs 50 are seen to extend outwardly from face 42 in an axial direction. The spacing legs 50 are seen to have a pair of opposed major sides and a pair of opposed minor sides. The major sides of legs 50 extend axially and distally. The distal minor side of each leg 50 is free while the proximal minor side is connected to the face 42. At least one spacing leg is utilized, preferably four.

The tubular member 20 is also seen to have annular members 80 circumferentially displaced about the exterior of tubular member 20. The circumferential annular members 80 provide a surface for engaging sutured tissue. The annular members 80 may be continuous or may be segmented. The number of circumferential annular members 80 present on the tubular body 20 will be sufficient to provide effective tissue retention; typically about two to about three, and preferably about three annular members 80 are present on the tubular member 20, although more or less may be present. The height of the annular members 80 above the exterior surface of the member 20 will be sufficient to provide effective tissue retention. If one were willing to accept whatever disadvantages may be present, if any, the annular rings 80 may be eliminated from the tubular body 20 or may be replaced with radially extending projections or protuberances.

The anvil bushing 10 is seen to have a proximal flange 60 having face 62 extending from the proximal end of tubular member 20. Face 62 is seen to be parallel to face 42 and both faces 42 and 62 are perpendicular to the longitudinal axis of the bushing 10. The diameter of flange 60 will be greater than the diameter of flange 40 to provide improved locatability within the intestine and to facilitate cutting by providing a larger surface for use as a cutting guide. The flanges 40 and 60 extend from the ends of tubular member 20 and may either be molded to the tubular member 20 if the anvil bushing is molded in one piece or may be mounted to the ends of the tubular member 20 if manufactured as separate pieces. The term "extend from" as used herein is defined to include both possibilities.

Tissue vent notches 70 are seen to be contained in, and extend through, the flange 60. The tissue vent notches 70 provide a pathway for tissue and fluids to vent into as tissue is being compressed when the gap 210 between the anvil 193 and the cartridge 170 of the circular stapler 100 is closed. Typically at least one vent notch 70 is present in the flange 60. Preferably, four vent notches 70 are utilized, located circumferentially at ninety degree intervals. The volume of the vent notches 70 will be sufficient to effectively provide tissue and fluid venting. A primary purpose of the vent notches 70 is to hold or retain tissue and prevent the tissue from slipping back over the anvil bushing 10.

The inner mucosal layer of an intestine consists of a slippery mucous membrane and the tissue notches 70 assist in retaining the tissue on the anvil bushing 10. Another function of the tissue notches 70 is to facilitate closure of the stapler 100. As the stapler 100 is closed, the intestinal tissue is compressed in the gap 210 between the distal end of the staple cartridge 190 and the anvil 193 of the anvil member 190. The tissue notches 70 provide a pathway for tissue, liquids and gases to flow into, thereby providing a venting which facilitates closure of the gap 210 between the distal end of the cartridge 170 and the anvil 193. As previously mentioned, the tissue notches 70 also assist in retaining the mucosa of the intestine.

The anvil bushing 10 may be utilized without legs 50 or without tissue notches 70, of course the attendant advantages of these features would not be present. For example, the bushing 10 could have flanges 40 and 60 without both legs 50 and notches 70, or, flanges 40 and 60 with notches 70 and without legs 50.

Referring to FIG. 4, the anvil bushing 10 of the present invention is seen mounted to a conventional circular stapler 100. The circular stapler 100 has proximal handle 110 mounted to an elongated tubular frame 150. Mounted to the distal end 155 of the elongate tubular frame 150 is the cartridge head 170. The cartridge head 170 contains a plurality of conventional staples 175 (not shown) arranged in a circular array to provide concentric rows of formed staples. The cartridge 170 also contains a cylindrical, circular knife 176 (not shown) having a cutting edge 179 for cutting tissue interior to the rows of formed staples. The handle 110 is seen to have mounted to its proximal end the knob 120 which can be rotated to increase or decrease the gap 210 between the cartridge head 170 and the anvil member 190. Also mounted to the handle 110 is the actuating lever 130 for actuating the driving of the staples 175 and the engagement of the knife 176. Extending from the cartridge 170 is the trocar shaft 180. The trocar shaft 180 is moveable, axially, distally and proximally by rotating the knob 120 either clockwise or counterclockwise.

As can be seen in FIG. 4 and FIG. 4A, the anvil member 190 is seen to be a cylindrical member having a tapered distal end 191 and a flat proximal end 192 for mounting circular, conventional anvil 193. Anvil 193 is seen to have forming cavities 194 for forming the ends of staples 175. Mounted to the proximal end 192 of anvil member 190 is the anvil member shaft 196 which extends axially from cavity 195 contained in the proximal end 192 of member anvil 190. The anvil shaft 196 is a cylindrical, tubular member which is mounted on the trocar shaft 180. Concentrically mounted in the cavity 195 on the interior side of the anvil 193 is the breakaway washer 200. The breakaway washer 200 is sized to engage the cutting edge 179 of circular knife 176 when the knife 176 is actuated. Preferably, the washer 200 is designed to split (i.e., the yield point is exceeded) when engaged by the knife 176 such that an inner annular section is disengaged from the washer 200 while an outer annular portion of the washer remains engaged in the cavity 195. Also concentrically mounted in the cavity 175 is the shoulder 212. The shoulder 212 is seen to be a tubular member having internal passage 215 and proximal face 214. The anvil shaft 196 is concentrically mounted to anvil member 190 through passage 215 in the shoulder 212.

Figure 6:
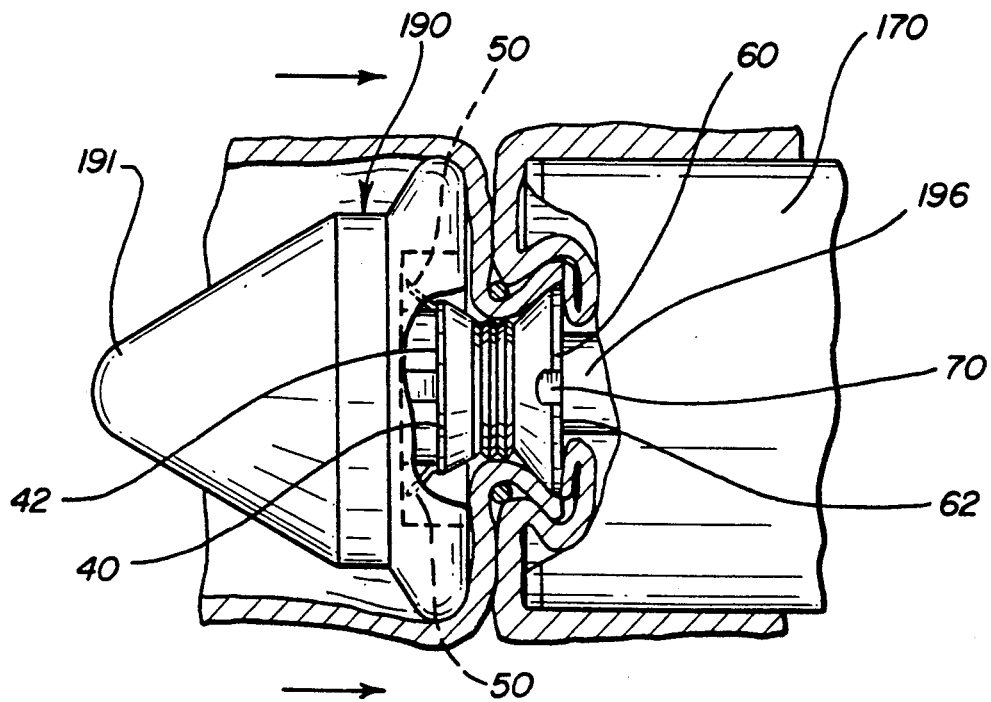
FIG. 6 illustrates the anvil bushing of FIG. 5 after the anvil gap has been closed and immediately prior to actuation of the staples and cutting blade.

The anvil bushing 10 is mounted on the shaft 196 by sliding the distal end of the bushing 10 onto the shaft 196 and positioning the bushing 10 such that the distal ends of legs 50 are in contact with the proximal face 214 of the shoulder 212, thereby properly locating the anvil bushing on the anvil shaft 196. The face 42 will typically be located a sufficient distance from face 214 to effectively allow bushing 10 to function. Preferably, the face 42 of distal flange 40 of the bushing 10 will be about 0.0625 inches from the face 214 when properly positioned. When the anvil member 190 is mounted onto the trocar shaft 180 by concentrically mounting the anvil shaft 196 onto the trocar shaft 180, the circular stapler is ready for use. Referring to FIG. 6, as the gap 210 is closed by actuating the knob 120, the proximal flange face 62 of the bushing 10 will come into contact with the distal face of the cartridge 170 thereby causing the bushing 10 to slide distally with respect to the anvil member 190 on the anvil shaft 196. As the bushing 10 slides, the legs 50 displace radially outward over the proximal face 214 and about the shoulder 212. The gap 210 can be decreased until the distal flange face 42 of the bushing 10 comes in contact with the proximal face 214 of the shoulder 212 at which point the bushing 10 will begin to compress.

The interior passage 30 of the bushing 10 is sufficiently sized to effectively provide a frictional fit between the interior of tubular member 20 and the exterior of anvil shaft 196. The dimension of the interior passage 30 will vary with the size of the anvil shaft 196. However, preferably, the diameter of passage 30 will be about 0.275 inches to about 0.281 inches, more preferably about 0.281 inches. Similarly, the other dimensions of anvil bushing 10 will vary with the size of the particular circular stapler employed and will similarly be sufficient to allow the bushing 10 to function effectively. Preferably, the length of the bushing 10 (not including the legs 50) will be about 0.295 inches to about 0.310 inches, more preferably 0.30 inches. Preferably, the diameter of the flange 40 will typically range from about 0.435 inches to about 0.444 inches, more preferably about 0.440 inches. The diameter of the flange 60 will preferably be from about 0.520 inches to about 0.530 inches, more preferably about 0.525 inches. The overall length of the bushing 10 will preferably be about 0.430 inches to about 0.450 inches, preferably about 0.440 inches.

Figure 5:
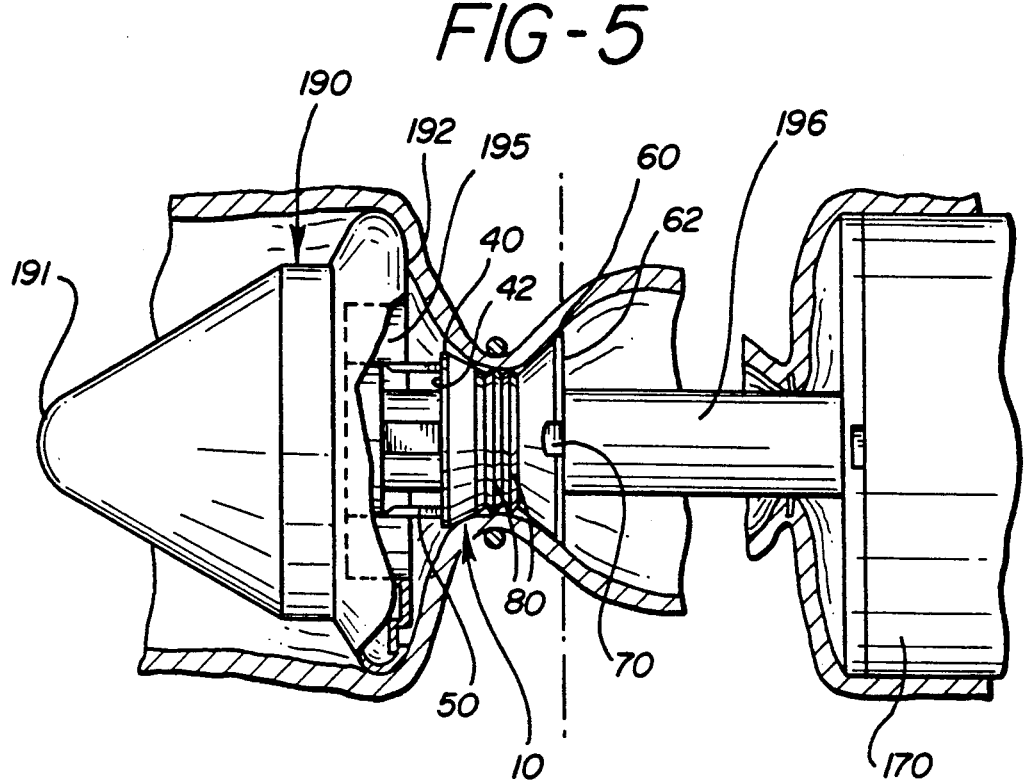
FIG. 5 illustrates the anvil bushing of the present invention mounted on a circular stapler anvil shaft in a sectional view of an intestine during an anastomosis prior to closing the anvil gap.

The anvil bushing 10 of the present invention may be used with a circular stapler 100 to perform an anastomosis in the following manner. After a patient has been prepared and anesthetized in accordance with conventional surgical techniques, the surgeon, using conventional surgical techniques, inserts the anvil member 190 and the cartridge 170 of a circular stapler 100 into a section of intestine proximate to a section of intestine targeted for removal. The gap 210 is typically opened to a maximum. Prior to inserting the anvil member 190 and cartridge 170 into the section of intestine, the surgeon places the anvil bushing 10 onto the anvil shaft 196 by sliding the distal end of the bushing 10 onto the anvil shaft 196 and positioning the anvil bushing on the anvil shaft 196 by locating the anvil bushing 10 such that the leg members 50 touch the proximal face 214 of the shoulder 212. The surgeon then ties a section of the intestine to the anvil bushing 10 using a conventional suture or suture loop such that the sutured intestine contacts the annular members 80. The surgeon then locates the flange 60 and then cuts the intestine using the proximal flange face 62 of the anvil bushing 10 as a cutting guide. The proximal flange 60 of the anvil bushing 10 has a larger diameter than the distal flange 40. The presence of the larger flange 60 enables the surgeon to readily identify the proximal flange face 62 of the bushing 10 and further facilitates cutting. Next, referring to FIGS. 5 and 6, the target section of intestine is surgically removed and the end of the intestine proximate to the target section that has been removed is tied to the anvil shaft 196 using conventional suturing methods such as a purse string tie. Then, the two sections of intestine are stapled and an interior piece is simultaneously cut by actuating the lever 130 of the stapler 100 causing staples 175 to be driven from the cartridge head 170 into the cavities 194 of anvil 192 thereby forming the staples and simultaneously driving the knife 176 forward and cutting an interior section of intestine adjacent to the anvil 192. The anvil member 190, the cartridge head 170, the stapler 100 and the cut pieces of intestine ends and sutures along with the anvil bushing 10 are removed from the patient. The anastomosis is then completed and any access openings are sutured or stapled in accordance with conventional surgical procedures.

A preferred method of using the anvil bushing 10 of the present invention is with a double staple technique wherein a target section of lumen, or specimen, is cut out from the intestine after stapling on both sides of the section with double rows of staples. The anvil member 190, having the anvil bushing 10 properly mounted thereto, is then inserted into the proximal lumen adjacent to the proximal staple line after making an incision in the bowel lumen. The lumen is then secured to the bushing 10 using a suture, preferably a preformed loop suture such as an ENDOLOOP ® suture manufactured by ETHICON, Inc., Somerville, N.J. Redundant tissue is then trimmed using flange 60 as a cutting guide. Next, the cartridge 190 and distal end 155 of frame 150 of the stapler 100 are inserted into the anus of the patient and positioned distal to the distal staple line in the lumen. The trocar shaft 180 of the stapler is extended through the lumen adjacent to the distal staple line. Then, the trocar shaft 180 is inserted into the anvil shaft 196. Next, the two sections of intestine are stapled as previously described and sections of cut intestine containing staples along with any section of breakaway washer 200 are removed along with the stapler 100 from the intestine.

A conventional anvil bushing 300 of the prior art is illustrated in FIG. 3. This anvil bushing 300 is seen to have a proximal flange 302 and a distal flange 310 having equal diameters. The bushing has a cylindrical member body 320 and an axial passage 325. The exterior of member 320 is seen to have a series of radially extending conical protuberances 330 extending therefrom to serve as an aid in retaining tissue on the exterior of the member 320. It is seen that the anvil bushing 300 does not have a means for locating the bushing on an anvil shaft and does not have tissue notches for facilitating closure of a stapler and for providing enhanced tissue retention.

In contrast, the anvil bushing 10 of the present invention has numerous advantages. The tissue vent notches 70 contained in the flange 60 allow tissue and fluids to flow while the gap 210 is being shortened or closed. Closing a gap 210 in a circular stapler 100 typically results in the compression of the tissue and fluids within the gap 210. This venting feature of the anvil bushing 10 typically reduces the force required to close the gap 210. Another advantage of the bushing 10 of the present invention is that the flange 60 is seen to have a larger radius or diameter than the flange 40. This allows the surgeon to more readily locate the flange 60 by palpation or otherwise and to further facilitate its use as a cutting guide. In addition, the bushing 10 is seen to have the distally extending leg members 50 extending from the flange 40 which assist the surgeon in properly positioning and locating the bushing 10 on the anvil shaft 196. Yet another advantage of the bushing 10 is that the tissue notches 70 facilitate grasping and retention of the slippery interior mucosal layer of the intestine.

The anvil bushing 10 may be manufactured using conventional manufacturing techniques including molding, casting, stamping, machining and the like. The anvil bushing 10 of the present invention may be made from any medical grade polymeric material having sufficient mechanical and biocompatiblity properties effective to allow the anvil bushing to function. It is particularly preferred to use biocompatible polymeric materials containing a radio-opaque filler such as Kraton ® styrene block copolymer containing barium sulfate available from RTP Company, Winona, Minn. 55987.

EXAMPLE 1

The following example is illustrative of the principles and practice of the present invention although not limited thereto.

A mammal was prepared for surgery and anesthetized in accordance with conventional surgical procedures. A Verres needle was inserted into the abdominal cavity at the umbilicus. The abdomen was insufflated with $CO_2$. Insufflation was maintained during the procedure. A conventional 10/11 mm trocar was inserted at the umbilicus. A conventional 10 mm endoscope was inserted through a 10/11 mm trocar and connected to a light projector. A camera was mounted to the head of the endoscope. The camera allowed viewing (using a TV monitor) and recording (using a VCR) of the abdominal cavity and of all subsequent trocar insertions.

Secondary 5 mm or 10 mm conventional trocars were inserted as necessary in the caudal part of the abdomen to allow visualization and mobilization of the descending colon. The mesocolon was isolated and ligated or coagulated using conventional clips or electrocautery.

A stapled anastomosis was performed in the following manner: The bowel was transected with a conventional endoscopic linear cutter. The proximal staple line was trimmed to allow insertion of the anvil member 190. The anvil member 190 was detached from the stapler 100 and inserted through a trocar port. The anvil member 190 with tissue retaining anvil bushing 10 was positioned in the proximal portion of bowel and secured with an ENDOLOOP ® suture. Excess tissue was trimmed, using the larger flange 60 of the anvil bushing as a cutting guide. The distal end of circular stapler 100 was inserted through the anus. The trocar shaft 180 was extended beside the distal staple line. The anvil shaft 196 was placed over the trocar shaft 180, aligned, snapped into place and tested for security. The gap 210 of stapler 100 was closed, tightened to the appropriate staple height setting, and fired to perform the colonic anastomosis. The stapler 100 was removed from the colon. The resultant tissue donuts were examined for completeness. The colonic anastomosis was checked for patency and leakage.

Although this invention has been shown and described with respect to detailed embodiments thereof, it will be understood by those skilled in the art that various changes in form and detail thereof maybe made without departing from the spirit and scope of the claimed invention.

WHAT IS CLAIMED IS:

1. An anvil bushing for a surgical, circular stapler, the anvil bushing comprising:

a tubular member having a proximal end and a distal end, and an exterior surface, said tubular member having an axial passageway therethrough for mounting onto a shaft, a second flange having a first diameter extending from the distal end of the tubular member;

a second flange having a first diameter extending from the proximal end of the tubular member, the second diameter being greater than the first diameter;

tissue notch means contained in the second flange providing a pathway for tissue; and means for locating the anvil in a position on the anvil shaft, said locating means mounted to the first flange.

2. The anvil bushing of claim 1, wherein the tissue notch means comprises at least one opening extending through the second flange.

3. The anvil bushing of claim 1, wherein the tissue notch means comprises a plurality of openings extending through the second flange.

4. The anvil busing of claim 1, wherein the locating means comprises at least one leg member extending axially from the first flange.

5. The anvil bushing of claim 1, wherein the locating means comprises a plurality of leg members extending from the first flange.

6. The anvil bushing of claim 1 wherein the tubular member further comprises tissue engagement means extending from the exterior surface thereof.

7. The anvil bushing of claim 6 wherein the engagement means comprises at least one protuberance.

8. The anvil bushing of claim 6 wherein the engagement means comprises at least one annular member.

9. The anvil bushing of claim 1 wherein the passage through the tubular member comprises a cylindrical configuration.

10. An anvil bushing for a surgical, circular stapler, the anvil bushing comprising:

a tubular member having a proximal end and a distal end, and an exterior surface, said tubular member having an axial passageway therethrough for mounting onto a shaft, a second flange having a first diameter extending from the distal end of the tubular member;

a second flange having a first diameter extending from the proximal end of the tubular member, the second diameter being greater than the first diameter; and, tissue notch means contained in the second flange providing a pathway for tissue.

11. The anvil bushing of claim 10, wherein the tissue notch means comprises at least one opening extending through the second flange.

12. The anvil bushing of claim 10, wherein the tissue notch means comprises a plurality of openings extending through the second flange.

13. The combination comprising:

a circular stapler; and, an anvil bushing, wherein the anvil bushing comprises a tubular member having a proximal end and a distal end, and an exterior surface, said tubular member having an axial passageway therethrough for mounting onto a shaft;

a second flange having a first diameter extending from the distal end of the tubular member;

a second flange having a first diameter extending from the proximal end of the tubular member, the second diameter being greater than the first diameter;

tissue notch means contained in the second flange providing a pathway for tissue; and means for locating the anvil in a position on the anvil shaft, said locating means mounted to the first flange.

14. The anvil bushing of claim 13, wherein the tissue notch means comprises at least one opening extending through the second flange.

15. The anvil bushing of claim 13, wherein the tissue notch means comprises a plurality of openings extending through the second flange.

16. The anvil busing of claim 13, wherein the locating means comprises at least one leg member extending axially from the first flange.

17. The anvil bushing of claim 13, wherein the locating means comprises a plurality of leg members extending from the first flange.

18. The anvil bushing of claim 13 wherein the tubular member further comprises tissue engagement means extending from the exterior surface thereof.

19. The anvil bushing of claim 18 wherein the engagement means comprises at least one protuberance.

20. The anvil bushing of claim 18 wherein the engagement means comprises at least one annular member.

21. The anvil bushing of claim 13 wherein the passage through the tubular member comprises a cylindrical configuration.

22. A method of using a circular stapler having an anvil, an anvil shaft, a staple cartridge and an actuating means to connect sections of intestine, comprising:

positioning an anvil bushing onto the anvil shaft, wherein the bushing comprises: a tubular member having a proximal end and a distal end, and an exterior surface, said tubular member having an axial passageway therethrough for mounting onto a shaft, a first having a first diameter flange extending from the distal end of the tubular member; a second flange having a second diameter extending from the proximal end of the tubular member, the second diameter being greater than the first diameter; tissue notch means contained in the second flange providing a pathway for tissue; and means for locating the anvil in a position on the anvil shaft, said locating means mounted to the first flange;

inserting the anvil and cartridge into adjacent sections of an intestine;

tying at least one section of the intestine to the bushing; and, actuating the actuating means to staple the sections of the intestine together.

* * * * *